US00PP25853P3

(12) United States Plant Patent
Schoone

(10) Patent No.: US PP25,853 P3
(45) Date of Patent: Sep. 1, 2015

(54) *PHALAENOPSIS* ORCHID PLANT NAMED 'EYE WONDER'

(50) Latin Name: *Phalaenopsis hybrida*
Varietal Denomination: Eye Wonder

(71) Applicant: Floricultura, Heemskerk (NL)

(72) Inventor: René Schoone, Assendelft (NL)

(73) Assignee: FLORICULTURA, Heemskerk (NL)

( * ) Notice: Subject to any disclaimer, the term of this patent is extended or adjusted under 35 U.S.C. 154(b) by 156 days.

(21) Appl. No.: 13/986,325

(22) Filed: Apr. 22, 2013

(65) Prior Publication Data

US 2013/0291253 P1 Oct. 31, 2013

Related U.S. Application Data

(60) Provisional application No. 61/638,009, filed on Apr. 25, 2012.

(30) Foreign Application Priority Data

Apr. 26, 2012 (NL) ..... PBR OPS905

(51) Int. Cl.
*A01H 5/00* (2006.01)
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — Susan McCormick Ewoldt
(74) *Attorney, Agent, or Firm* — Foley & Lardner LLP; Sunit Talapatra

(57) ABSTRACT

A new and distinct *Phalaenopsis* plant named 'Eye Wonder' particularly characterized by flowers which are light purple with a yellow/green haze; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Eye Wonder'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Eye Wonder'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Eye Wonder' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Eye Wonder' originated from a cross made by the inventor in 1999 in Strengweg, Heemskerk, The Netherlands. The female or seed parent is the *Phalaenopsis* cultivar designated 'Romance Valentine', unpatented. The male or pollen parent is the *Phalaenopsis* cultivar designated 'Barbara Buddha', unpatented. The new *Phalaenopsis* 'Eye Wonder' was discovered and selected by the inventor as a single flowering plant within the progeny of the stated cross in a controlled environment in 2007 in Strengweg, Heemskerk, The Netherlands.

Asexual reproduction of the new *Phalaenopsis* cultivar by tissue culture was first performed in November, 2007 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true to type.

BRIEF DESCRIPTION OF THE INVENTION

The following traits have been repeatedly observed and are determined to be unique characteristics of 'Eye Wonder', which in combination distinguish this *Phalaenopsis* as a new and distinct cultivar:

1. flowers which are light purple with a yellow/green haze;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Eye Wonder', the female parent 'Romance Valentine' has dark pink flowers and the male parent 'Barbara Buddha' has yellow/bronze colored flowers, whereas the flowers of 'Eye Wonder' are light purple with a yellow/green haze.

Presently, the commercial cultivar to which 'Eye Wonder' can be meaningfully compared is 'Lark Song' (unpatented). The size of the plant of 'Lark Song' is larger. The color of the flowers of 'Eye Wonder' is darker purple than the color of 'Lark Song'. 'Eye Wonder' also haze a yellow/green haze on the flower. The main color of the labellum of 'Eye Wonder' is purple, whereas the main color of the labellum of 'Lark Song' is white.

BRIEF DESCRIPTION OF THE PHOTOGRAPHS

The accompanying photographs illustrate the overall appearance of the new *Phalaenopsis* 'Eye Wonder' showing the colors as true as is reasonably possible with colored reproductions of this type. Colors in the photographs may differ slightly from the color values cited in the detailed botanical description, which accurately describe the color of 'Eye Wonder'.

DETAILED BOTANICAL DESCRIPTION

Figure 1:
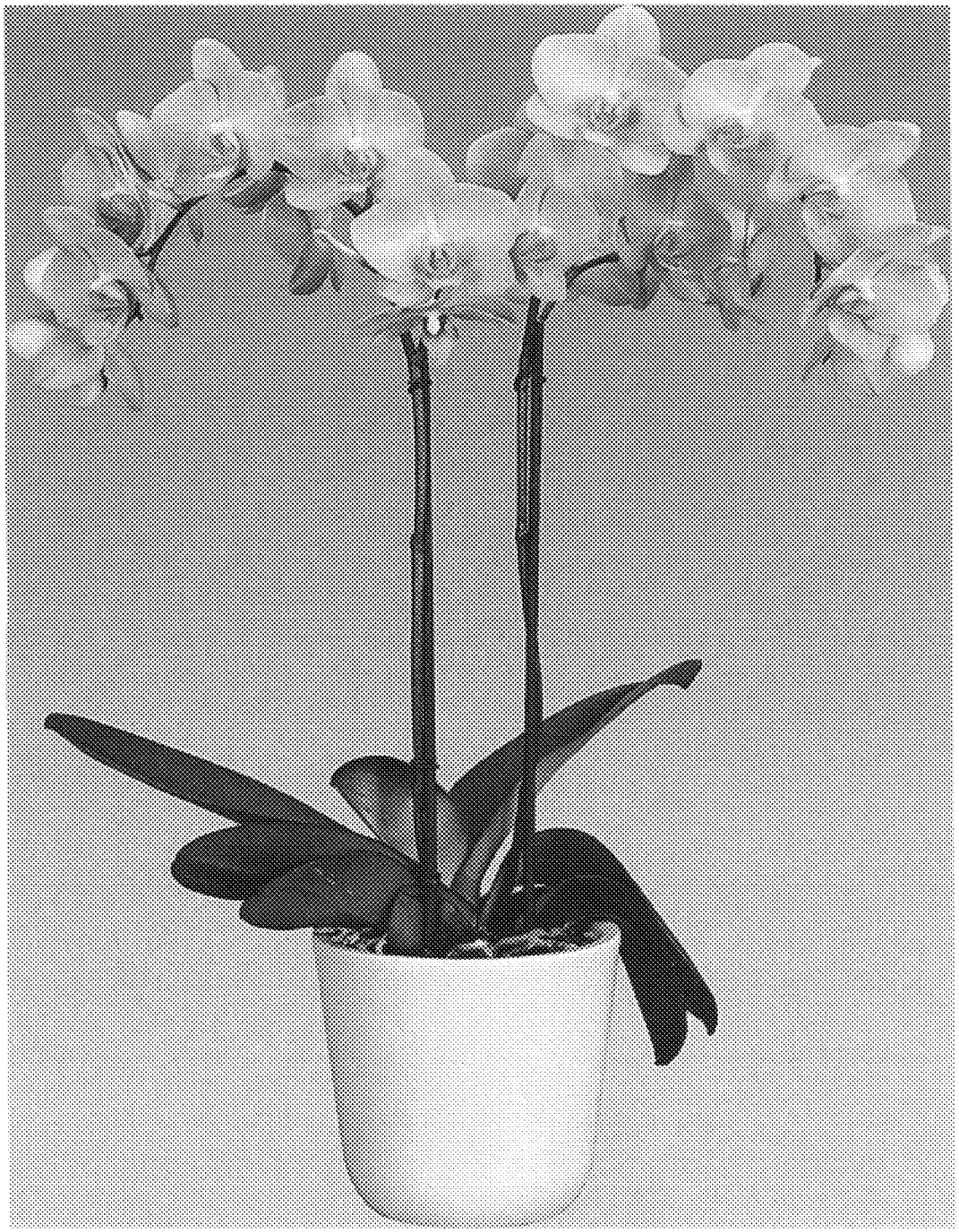
FIG. 1 shows a side view perspective of a typical flowering plant of 'Eye Wonder' in a 12 cm pot, at 16 months of age.

The new *Phalaenopsis* cultivar 'Eye Wonder' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Eye Wonder' as grown in a greenhouse in Strengweg, Heemskerk, The Netherlands, under conditions which closely approximate those generally used in commercial practice. Initially, the ideal temperature to grow plants of 'Eye Wonder' is 27° C. during the day and at night. Then, during the flowering phase of 'Eye Wonder', the ideal growing temperature is 20-22° C. during the day and 18° C. at night. Light levels for growing 'Eye Wonder' are a minimum of 5,000 lux and a maximum of 10,000 lux. A balanced fertilizer with level of 200 ppm N, 87 ppm P, 168 ppm K is applied. Duration of growth of 'Eye Wonder' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Eye Wonder' plants described is 12 months after potting.

Classification:

*Botanical.—Phalaenopsis hybrida.*

Parentage:

*Female or seed parent.—Phalaenopsis* cultivar designated 'Romance Valentine', unpatented.

*Male or pollen parent.—Phalaenopsis* cultivar designated 'Barbara Buddha', unpatented.

Propagation:

*Type*.—Tissue culture.

*Rooting habit and description*.—Fleshy; approximately 3 mm-7 mm wide and yellow/green in color (RHS 148D); freely branching. It takes 12 weeks for plants growing in tissue culture to initiate roots.

Plant:

*Size at maturity*.—Height: about 60 cm. Spread: about 60 cm.

*Growth habit*.—Standard; dark green leaves and a relatively normal raceme.

*Vigor*.—Moderate.

*Crop time*.—Following asexual propagation, at about 26 weeks 2 leaves appear; at about 30 weeks 3-4 leaves appear; after a cold treatment of about 4-8 weeks at a temperature of about 19° C. about 1-2 racemes with flowers appear.

Foliage:

*Quantity per plant*.—About 6 to 8 leaves are produced before flowering.

*Arrangement and attachment*.—Half up/horizontal and on two sides.

*Overall shape of leaf*.—Oval, the tip is blunt and asymmetric.

*Texture* (*upper & underside*).—Smooth and leathery.

*Pubescence*.—None.

*Mature leaf length*.—About 15 to 24 cm.

*Mature leaf width*.—About 6 to 10 mm.

*Mature leaf thickness*.—About 1.5 mm.

*Mature leaf color*.—Upper side: green (RHS 137A), parts of the edges are green (RHS 137C/RHS 137B). Under side: yellow/green (RHS 146B).

*Leaf base*.—Acute.

*Margin*.—Entire.

*Venation*.—Pattern: parallel. Color of midvein: upper side: green (RHS 139A) under side: yellow/green (RHS 145B).

Inflorescence description:

*Appearance*.—Upright to slightly pendant, racemose inflorescence with bilaterally symmetrical flowers that open in succession beginning with the lowermost flower.

*Raceme*.—Quantity per plant: about 1 to 2. Number of flowers per raceme: about 7 to 12. Length: about 49 to 55 cm.

*Peduncle*.—Diameter: about 4 mm. Strength: strong. Aspect: upright. Texture: glabrous and smooth. Color: green (RHS N137D) which runs into RHS 137D.

*Buds*.—Height (from base to tip): about 21 mm to 26 mm. Diameter (at midpoint): about 15 mm to 21 mm. Shape: egg-shaped. Color: yellow/green (RHS 154A) which runs into purple (RHS 72A).

*Flowering time*.—For an untreated plant (flowering plant that has not undergone cold-treatment where the plant grows at a temperature of 18° C. to 19° C. for about 4 to 8 weeks after a period of about 30 weeks at a temperature of 25° C.), 1-2 racemes appear with flower buds and flowers. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
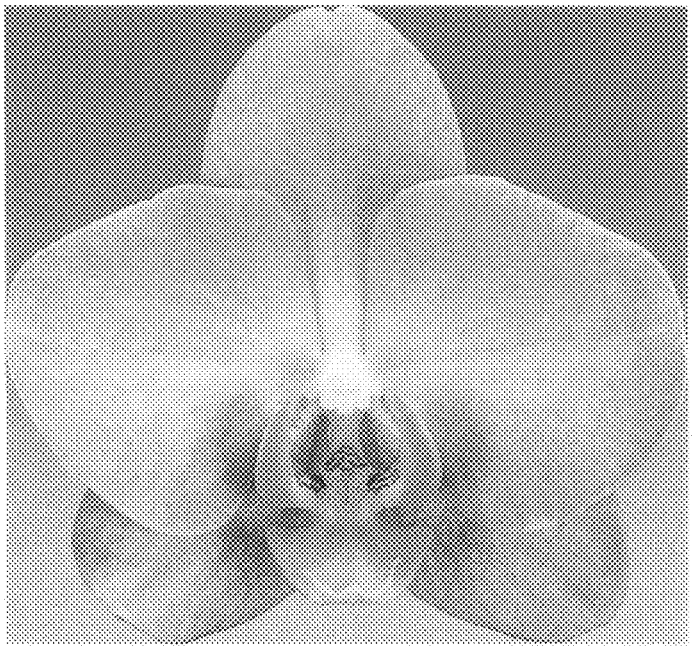
FIG. 2 shows a close-up view of a typical flower of 'Eye Wonder'.
Figure 3:
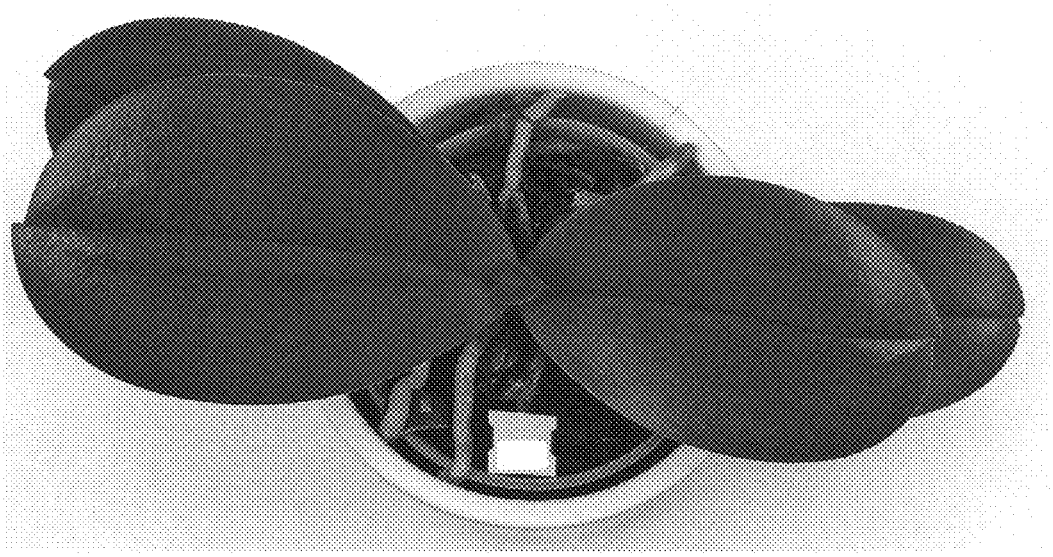
FIG. 3 shows a close-up view of the typical leaves of 'Eye Wonder'.

*Flower*.—Rate of opening: Flowers fully opened about 2 to 3 days after petal and sepal separation. Orientation at opening: slanted upward and outward. Shape: Typical shape of *Phalaenopsis* orchid; see FIG. 2. Size (of single bloom): Height: about 56 mm to 69 mm. Diameter: about 65 mm to 78 mm. Quantity and arrangement: three petals and three sepals that are trimerous, overlapping and arranged in 2 whorls. Petals are more pronounced than sepals.

*Petals*.—Arrangement: Inner whorl comprises 3 petals: 2 lateral petals and labellum. 2 lateral petals: Overall shape: broadly ovate, little triangular and weakly cupped. Apex: oval, a little flat and weakly undulate. Margin: entire and weakly undulate. Base: broadly ovate. Length: about 35 mm. Width: about 33 mm. Texture: Upper surface: smooth and satiny. Under surface: smooth and satiny. Color (when fully opened): upper side: main color is purple (RHS N78D). At base and the edges white (RHS N155B), with a light yellow/green haze (RHS 145D) and spots at the base (RHS N78C). Under surface: main color is purple (a combination of RHS N78D and RHS N78C). From base and in center yellow/green (RHS 145D). Labellum: Overall representation: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire and weakly undulate. Apex: oval. Length: about 22 mm. Width (not flattened): about 18 mm. Depth of tube created by lateral lobes of labellum: about 10 mm. Texture: Upper and under surface: smooth and satiny. Color (when fully opened): Midlobe: upper surface: main color is purple (RHS N78C. From base and on the sides orange/red (RHS N34D) and at the base a little yellow (RHS 13A). Under surface: main color is purple (N78D) with a white haze in the center (RHS N155B).On sides orange/red (RHS N34D) and very edge RHS N34A. Lateral lobes: upper surface: white (RHS NN155B) with yellow (RHS 13A) and purple/red spots and stripes (RHS 60A). Lower edge is orange/red (RHS N34D). At the top of the lob purple (RHS N78B). Under surface: base is white (RHS N155B) which runs into purple (RHS N78C). Lower edge is orange/red (RHS N34A) with yellow (RHS 13C). Cirrhi: about 7 mm. color: from purple (RHS N78D) to white (RHS N155C) to yellow (RHS 13D). Pestle (Callosities): Length: about 6 mm. Width (not flattened): about 5 mm. Color: main color is white (NN155C). Top and sides are yellow (RHS 13A). Spots are RHS red/purple (RHS 60A).

*Sepals*.—Arrangement: Outer whorl comprises 3 sepals, one dorsal and two lateral sepals. Overall shape: elliptical and weakly cupped. Margin: entire and weakly undulate. Length: about 36 mm. Width: about 27 mm. Apex: oval; lateral: small point, dorsal: small notch. Texture: Upper and under surface: smooth and satiny. Color (when fully opened): main color dorsal and lateral is purple (RHS N78D). At base dorsal sepal some small purple spots (RHS 77D) and in center a green haze (RHS 145C). At base lateral sepal white (RHS N155B) which runs into purple (RHS 77D) with spots (RHS N78A). Under surface: main color dorsal sepals is purple (RHS N78B) with in the center a light yellow/green haze (RHS 145A). Main color and edges lateral sepals is purple (RHS N77B). At the base in the center a yellow/green haze (RHS 145B).

*Pedicel*.—Length: about 38 mm. Diameter: about 4 mm. Texture: glabrous and smooth. Color: at the base yellow/green (RHS 146A, in the middle yellow/green (RHS 146D) and close to flower yellow/green (RHS 145D).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 11 mm. Diameter: about 7 mm. Color: white (RHS NN155C) with purple (RHS N78D).

*Pollinia*.—Quantity: two. Diameter: about 1 mm. Color: orange (RHS 26A).

*Ovary*.—Length: about 5 mm. Diameter: about 5 mm. Color: white (RHS N155B).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Eye Wonder', as illustrated and described herein.

* * * * *